(12) United States Patent
Chudasama et al.

(10) Patent No.: US 7,960,551 B2
(45) Date of Patent: Jun. 14, 2011

(54) COMPOUND

(75) Inventors: Reshma Chudasama, Stevenage (GB); Andrew Kennedy, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 872 days.

(21) Appl. No.: 11/672,536

(22) Filed: Feb. 8, 2007

(65) Prior Publication Data

US 2007/0281971 A1    Dec. 6, 2007

(51) Int. Cl.
*C07D 215/38*  (2006.01)
(52) U.S. Cl. ..................................... 546/159; 514/312
(58) Field of Classification Search .................. 546/159; 514/312

See application file for complete search history.

(56) References Cited

U.S. PATENT DOCUMENTS

| | | | |
|---|---|---|---|
| 4,026,897 A | 5/1977 | Nakagawa et al. | |
| 4,460,581 A | 7/1984 | Schromm et al. | |
| 4,894,219 A | 1/1990 | Baker et al. | |
| 4,992,474 A | 2/1991 | Skidmore et al. | |
| 5,621,010 A | 4/1997 | Sueda et al. | |
| 6,268,533 B1 | 7/2001 | Gao et al. | |
| 6,362,371 B1 | 3/2002 | Moran et al. | |
| 6,541,669 B1 | 4/2003 | Moran et al. | |
| 6,576,793 B1 | 6/2003 | Moran et al. | |
| 6,593,497 B1 | 7/2003 | Choi et al. | |
| 6,635,764 B2 | 10/2003 | Mammen et al. | |
| 6,653,323 B2 | 11/2003 | Moran et al. | |
| 6,670,376 B1 | 12/2003 | Moran et al. | |
| 6,693,202 B1 | 2/2004 | Aggen et al. | |
| 6,713,651 B1 | 3/2004 | Moran et al. | |
| 6,747,043 B2 | 6/2004 | Moran et al. | |
| 7,141,671 B2* | 11/2006 | Mammen et al. | 546/224 |
| 7,345,175 B2* | 3/2008 | Mammen et al. | 546/242 |
| 7,355,046 B2* | 4/2008 | Mammen et al. | 546/135 |
| 7,507,751 B2* | 3/2009 | Mammen et al. | 514/314 |
| 7,514,558 B2* | 4/2009 | Mammen et al. | 546/157 |
| 7,521,561 B2* | 4/2009 | Mammen et al. | 546/157 |
| 7,524,959 B2* | 4/2009 | Mammen et al. | 546/157 |
| 2003/0018019 A1 | 1/2003 | Meade et al. | |
| 2004/0167167 A1* | 8/2004 | Mammen et al. | 514/317 |
| 2004/0209860 A1* | 10/2004 | Mammen et al. | 514/183 |
| 2004/0209915 A1* | 10/2004 | Mammen et al. | 514/317 |
| 2004/0242622 A1 | 12/2004 | Mammen et al. | |
| 2005/0113417 A1 | 5/2005 | Mammen et al. | |
| 2005/0182092 A1 | 8/2005 | Chao et al. | |
| 2006/0035931 A1 | 2/2006 | Chao et al. | |
| 2006/0035933 A1 | 2/2006 | Mammen et al. | |
| 2006/0116398 A1 | 6/2006 | Mammen et al. | |
| 2006/0223858 A1* | 10/2006 | Mammen et al. | 514/317 |
| 2006/0223859 A1* | 10/2006 | Mammen et al. | 514/317 |
| 2006/0223860 A1* | 10/2006 | Mammen et al. | 514/317 |
| 2006/0229334 A1* | 10/2006 | Mammen et al. | 514/312 |
| 2007/0037984 A1* | 2/2007 | Mammen et al. | 546/153 |
| 2007/0088054 A1* | 4/2007 | Mammen et al. | 514/317 |
| 2007/0208176 A1* | 9/2007 | Mammen et al. | 546/153 |
| 2007/0276003 A1* | 11/2007 | Mammen et al. | 514/327 |
| 2008/0015220 A1* | 1/2008 | Mammen et al. | 514/312 |

FOREIGN PATENT DOCUMENTS

| | | |
|---|---|---|
| EP | 0073505 B1 | 3/1983 |
| EP | 0419397 B1 | 3/1991 |
| EP | 0747355 A1 | 12/1996 |
| EP | 0863141 B1 | 9/2001 |
| EP | 0930298 B1 | 12/2002 |
| WO | 93/20071 A1 | 10/1993 |
| WO | 95/06635 A1 | 3/1995 |
| WO | 9931086 A1 | 6/1999 |
| WO | 99/64031 A1 | 12/1999 |
| WO | 99/64035 A1 | 12/1999 |
| WO | 99/64043 A1 | 12/1999 |
| WO | 00/75114 A1 | 12/2000 |
| WO | 01/42212 A1 | 6/2001 |
| WO | 01/42213 A1 | 6/2001 |
| WO | 01/94319 A1 | 12/2001 |
| WO | 02/051841 A1 | 7/2002 |
| WO | 02/066422 A1 | 8/2002 |
| WO | 03/087097 A1 | 10/2003 |
| WO | 04/012684 A2 | 2/2004 |
| WO | 04/016578 A2 | 2/2004 |
| WO | 04/074246 A2 | 9/2004 |
| WO | 04/089892 A2 | 10/2004 |
| WO | 06/023454 A1 | 3/2006 |

OTHER PUBLICATIONS

Office Action in U.S. Appl. No. 10/779,157, dated Feb. 3, 2006.
Office Action in U.S. Appl. No. 10/778,290, dated Jul. 21, 2005.
Office Action in U.S. Appl. No. 10/778,290, dated Feb. 8, 2006.
Office Action in U.S. Appl. No. 10/778,290, dated Jul. 17, 2006.
Office Action in U.S. Appl. No. 10/778,290, dated Jan. 25, 2007.
Isogaya, et al., "Binding Pockets of the B1- and B2-Adrenergic Receptors for Subtype-Selective Agonists", Molecular Pharmacology, 56, pp. 875-885 (1999).
Milecki, et al., "Carbostyril Derivatives Having Potent B-Adrenergic Agonist Properties", J. Med. Chem., 30, pp. 1563-1566 (1987).
Naito, et al., "Selective Muscarinic Antagonist II. 1)Synthesis and Antimuscarinic Properties of Biphenylylcarbamate Derivatives", Chem. Pharm. Bull., vol. 46, No. 8, pp. 1286-1294 (1998).
"New long acting B2 agonists", Expert Opin. Ther. Patents, 13(2), pp. 273-277 (2003).
Office Action in U.S. Appl. No. 10/778,649, dated Mar. 7, 2007.
Summary of Peru Office Action from Agent dated Jun. 16, 2010.
Amended Claims dated Jul. 30, 2010 (Marked Copy) for Inclusion with Instructions for Responding to Peru Office Action (Aug. 9, 2010).
Amended Claims dated Jul. 30, 2010 (Clean Copy) for Inclusion with Instructions for Responding to Peru Office Action (Aug. 9, 2010).
Instruction Letter dated Aug. 9, 2010 enclosing instructions to Agent for Responding to Peru Office Action.

* cited by examiner

*Primary Examiner* — D. Margaret Seaman
(74) *Attorney, Agent, or Firm* — Robert J. Smith

(57) ABSTRACT

A succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof, for use in treating pulmonary disorders.

15 Claims, 7 Drawing Sheets

(Data are presented as 4000-700 cm$^{-1}$ (top) and 2000-700cm$^{-1}$ (bottom))

(Data are presented as 4000-700 cm$^{-1}$ (top) and 2000-700cm$^{-1}$ (bottom))

(Data are presented as 4000-700 cm$^{-1}$ (top) and 2000-700cm$^{-1}$ (bottom).)

Figure 10 - Dynamic Vapour Sorption Assessment of the succinate salt, Form 1
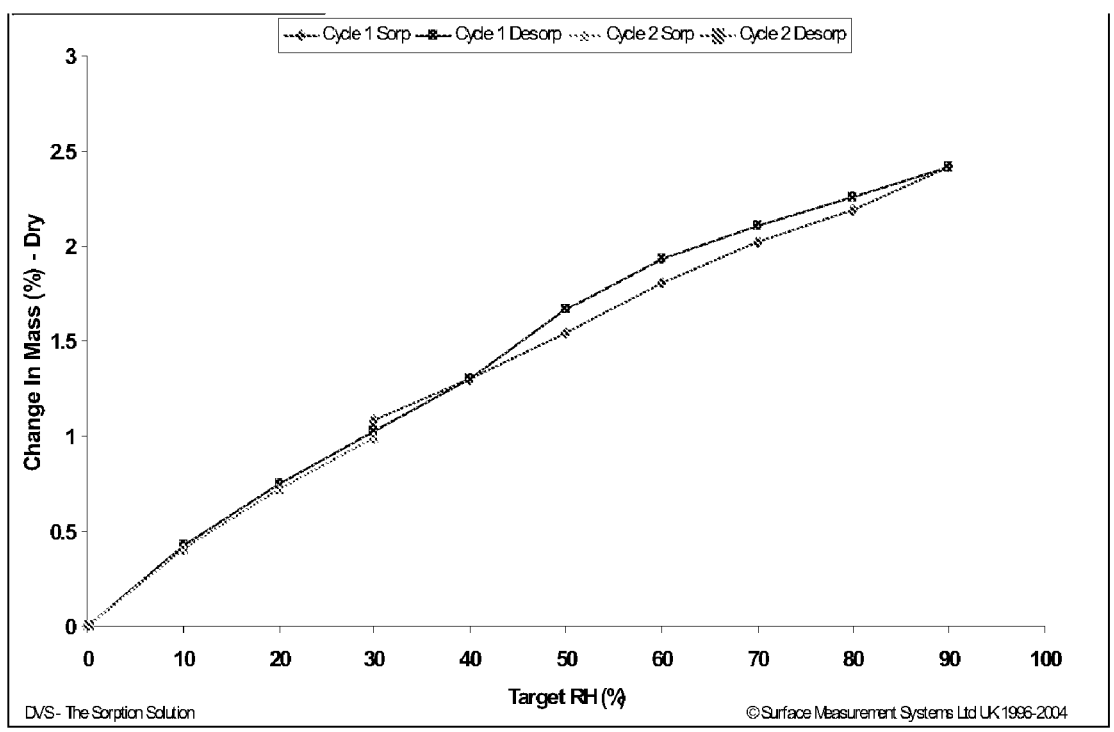

COMPOUND

CROSS-REFERENCE TO RELATED APPLICATIONS

This application claims priority to GB patent application No. 0602778.3 filed Feb. 10, 2006 in the United Kingdom.

BACKGROUND OF THE INVENTION

1. Field of the Invention

The present invention relates to a novel succinic acid salt of a biphenyl compound, in particular crystalline solid state forms of the succinic acid salt. The biphenyl compound is expected to be useful as a therapeutic agent for treating pulmonary disorders. This invention also relates to pharmaceutical compositions comprising the salt or prepared from this salt, processes and intermediates for preparing the salt and methods of using the salt to treat a pulmonary disorder.

2. State of the Art

International Patent application no PCT/US2004/004449, publication no. WO 2004/074246 A2 (Theravance Inc, South San Francisco, Calif., US) discloses novel biphenyl compounds that are useful as therapeutic agents for treating pulmonary disorders, such as chronic obstructive pulmonary disease (COPD) and asthma. In particular, the compound biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester is specifically disclosed in these applications as processing both muscarinic antagonist and $\beta_2$ adrenergic receptor agonist activity. The chemical structure of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester is represented by formula I:

International Patent application no PCT/US2004/004449, publication no. WO 2004/074246 A2 (Theravance Inc, South San Francisco, Calif., US), at page 135, as Example 35, describes the preparation of the compound of formula I, as the ditrifluoroacetate salt, in a lyophilised form.

International Patent application no PCT/US2005/029013, publication no. WO 2006/023454, filed 15 Aug. 2005, (Theravance Inc, South San Francisco, Calif., US) describes crystalline 1,2-ethanedisulfonic acid salts of the compound of formula I.

There remains the need to identify further stable, non-deliquescent, crystalline salt forms of the compound of formula I which have an acceptable level of hygroscopicity and a relatively high melting point.

SUMMARY OF THE INVENTION

The present invention provides a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, in particular a crystalline solid state form thereof, or a solvate thereof.

In one embodiment, a crystalline form of the salt of the present invention, hereinafter referred to as Form 1, has a melting point greater than about 170° C. and has been found not to be deliquescent, even when exposed to atmospheric moisture. Further crystalline salt forms, hereinafter referred to as Form 2 and 3, have also been identified.

Among other uses, a succinic acid salt of the compound of formula I is useful for preparing pharmaceutical compositions which are expected to be useful for treating pulmonary disorders. Accordingly, in a further embodiment, the present invention provides a pharmaceutical composition comprising a pharmaceutically acceptable carrier and a succinic acid salt of biphenyl-2-ylcarbamic acid 1-[2-(2-chloro-4-{[(R)-2-hy-

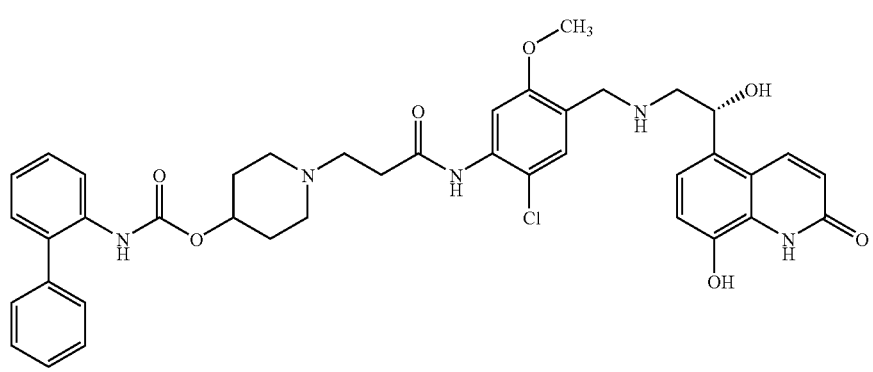

I

Therapeutic agents useful for treating pulmonary disorders are advantageously administered directly into the respiratory tract by inhalation. In this regard, several types of pharmaceutical inhalation devices have been developed for administering therapeutic agents by inhalation, including dry powder inhalers (DPI), metered-dose inhalers (MDI) and nebulizer inhalers. When preparing pharmaceutical compositions and formulations for use in such devices, it is highly desirable to have a crystalline form of the therapeutic agent that is neither hygroscopic nor deliquescent and which has a relatively high melting point (i.e. greater than about 150° C.), thereby allowing the material to be micronized without significant decomposition or loss of crystallinity.

droxy-2-(8-hydroxy-2-oxo-1,2-dihydroquinolin-5-yl)ethylamino]methyl}-5-methoxyphenylcarbamoyl)ethyl]piperidin-4-yl ester, in particular a crystalline solid state form thereof, or a solvate thereof.

In a particular embodiment, the pharmaceutical composition of this invention further comprises a steroidal anti-inflammatory agent, such as a cortecosteroid; a muscarinic antagonist or a phosphodiesterase-4 inhibitor; or a combination thereof.

In another embodiment, this invention provides a pharmaceutical composition comprising an aqueous isotonic saline solution comprising a succinic acid salt of biphenyl-2-ylcarbamic acid 1-[2-(2-chloro-4-{[(R)-2-hydroxy-2-(8-hydroxy- 2-oxo-1,2-dihydroquinolin-5-yl)ethylamino]methyl}-5-methoxyphenylcarbamoyl)ethyl]piperidin-4-yl ester, wherein the solution has a pH in the range of from about 4 to about 6.

In yet another embodiment, this invention provides a combination comprising:

(a) a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, in particular a crystalline solid state form thereof, or a solvate thereof; and (b) a steroidal anti-inflammatory agent.

The compound of formula I has both muscarinic antagonist and $\beta_2$ adrenergic receptor agonist activity. Accordingly, a succinic acid salt of this invention is expected to be useful as a therapeutic agent for treating pulmonary disorders, such as asthma and chronic obstructive pulmonary disease.

Accordingly, in one of its method aspects, this invention provides a method for treating a pulmonary disorder, the method comprising administering to a patient in need of treatment a therapeutically effective amount of a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof.

Additionally, in another of its method aspects, the invention provides a method of producing bronchodilation in a patient, the method comprising administering by inhalation to the patient a bronchodilation-producing amount of a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof.

This invention also provides a method of treating chronic obstructive pulmonary disease or asthma, the method comprising administering to a patient in need of treatment a therapeutically effective amount of a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof.

This invention is also directed to processes for preparing a succinic acid salt of the compound of formula I, in particular a crystalline form thereof.

Accordingly, this invention provides a process for preparing a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof; the process comprising contacting biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester with succinic acid.

This salt formation step may be conveniently carried out using the corresponding free base prepared from the corresponding tri-alkyl silyloxy-protected precursor, without the need for full isolation of the free base intermediate.

This invention is also directed to a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, or a crystalline solid state form thereof, or a solvate thereof, for use in therapy or as a medicament.

Additionally, this invention is directed to the use of a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, or a crystalline solid state form thereof, or a solvate thereof for the manufacture of a medicament; especially for the manufacture of a medicament for the treatment of a pulmonary disorder.

This invention is also directed to the use of:

(a) a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, or a crystalline solid state form thereof, or a solvate thereof; and (b) a steroidal anti-inflammatory agent;

in the manufacture of a medicament for the treatment of a pulmonary disorder.

This invention is also directed to a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, or a crystalline solid state form thereof, or a solvate thereof, in micronized form; and to pharmaceutical compositions comprising a pharmaceutically acceptable carrier and a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, or a crystalline solid state form thereof, or a solvate thereof, in micronized form.

BRIEF DESCRIPTION OF THE DRAWINGS

Various aspects of the present invention are illustrated by reference to the accompanying drawings.

FIG. 10 shows a Dynamic Vapour Sorption profile of a sample of the crystalline succinate salt (Form 1).

DETAILED DESCRIPTION OF THE INVENTION

Figure 1:
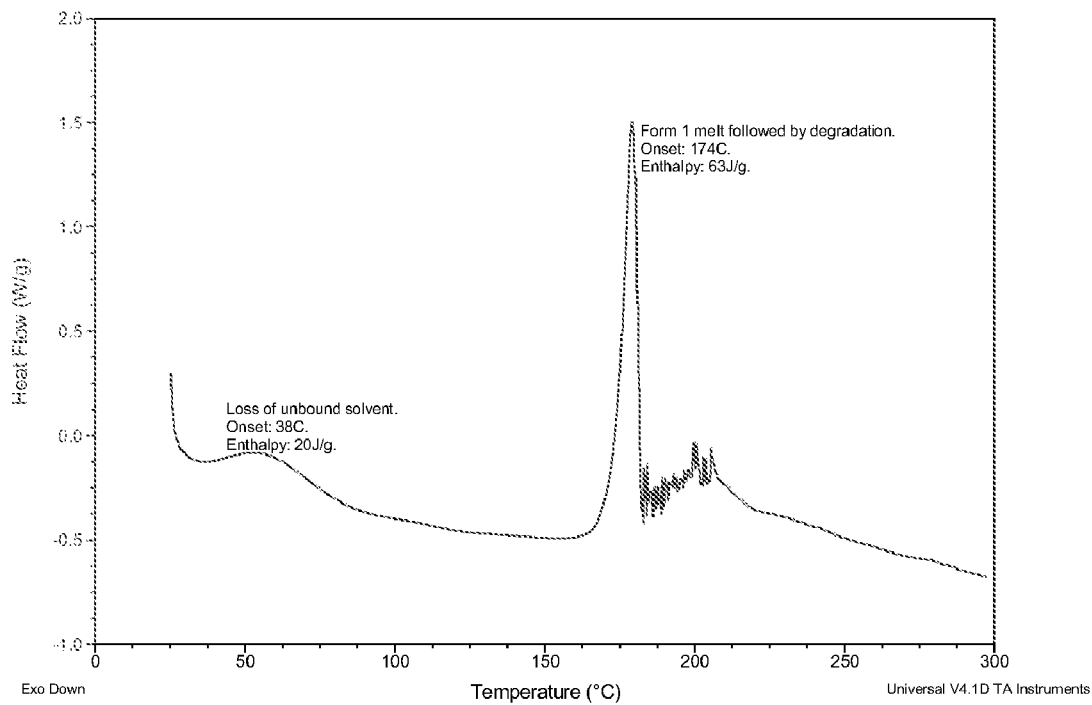
FIG. 1 shows a differential scanning calorimetry (DSC) trace for a sample of a first crystalline solid state form of a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl)]piperidin-4-yl ester of this invention, hereinafter referred to as Form 1.

This invention provides a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, in particular crystalline solid state forms (polymorphs) thereof and including solvates thereof. The crystalline succinic acid salt of the present invention may be present as one or more different distinct crystalline solid state forms. The present invention encompasses all such solid state forms.

In one embodiment, the present invention provides a first crystalline solid state form of the succinic acid salt of the compound of formula I: Form 1 thereof.

In a further embodiment, the present invention provides a second crystalline solid state form of the succinic acid salt of the compound of formula I: Form 2 thereof.

In a further embodiment, the present invention provides a third crystalline solid state form of the succinic acid salt of the compound of formula I: Form 3 thereof.

The active therapeutic agent in these salts (i.e., the compound of formula I) contains one chiral center having the (R) configuration. However, it will be understood by those skilled in the art that minor amounts of the (S) stereoisomer may be present in the compositions of this invention unless otherwise indicated, provided that any utility of the composition as a whole is not eliminated by the presence of such an isomer.

The compound of formula I has been named using the commercially-available AutoNom software (MDL, San Leandro, Calif.).

Definitions

When describing the compounds, compositions, methods and processes of this invention, the following terms have the following meanings unless otherwise indicated.

The term "melting point" as used herein means the melting onset temperature as observed by differential scanning calorimetry.

The term "micronized form" means a form of particles in which at least about 90% of the particles have a diameter of less than about 10 μm.

The term "solvate" means a complex or aggregate formed by one or more molecules of a solute, i.e. a succinic acid salt of the compound of formula I, and one or more molecules of a solvent. Such solvates (typically have a substantially fixed molar ratio of solute and solvent. This term also includes clathrates, including clathrates with water. Representative solvents include, by way of example, water, methanol, ethanol; isopropanol, acetic acid and the like. When the solvent is water, the solvate formed is a hydrate.

The term "therapeutically effective amount" means an amount sufficient to effect treatment when administered to a patient in need of treatment.

The term "treating" or "treatment" as used herein means the treating or treatment of a disease or medical condition (such as COPD) in a patient, such as a mammal (particularly a human) that includes:

(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The term "unit dosage form" refers to a physically discrete unit suitable for dosing a patient, i.e., each unit containing a predetermined quantity of a salt of the invention calculated to produce the desired therapeutic effect either alone or in combination with one or more additional units. For example, such unit dosage forms may be dry powder inhaler capsules or blister strips, a metered dose from a metered dose inhaler, capsules, tablets, pills, and the like.

Succinic Acid Salts of the Invention

A succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of this invention can be prepared from biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester and succinic acid.

A succinic acid salt of this invention typically contains between about 0.90 and about 1.10 molar equivalents of succinic acid per molar equivalent of the compound of formula I; including between about 0.95 and about 1.05 molar equivalents of succinic acid per molar equivalent of the compound of formula I. In a particular embodiment, the succinic acid salt of this invention consists about 1 molar equivalent of succinic acid per molar equivalent of the compound of formula I.

The molar ratio of succinic acid to biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester can be readily determined by various methods available to those skilled in the art. For example, such molar ratios can be readily determined by ¹H-NMR. Alternatively, elemental analysis can be used to determine the molar ratio.

Biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester may be conveniently prepared from the corresponding 2-tert-(Butyldimethylsilanyloxy)-protected precursor. This precursor may be deprotected using a source of fluoride ion such as cesium fluoride, with acetic acid, in a solvent such as methanol. The preparation of the tert-(Butyldimethylsilanyloxy)-protected precursor is described in International Patent application no PCT/US2004/004449, publication no. WO 2004/074246 A2, at page 135, Preparation 98.

Succinic acid is commercially available from, for example, Sigma-Aldrich Co. Ltd., Gillingham, UK. In one embodiment, the succinic acid has a purity greater than or equal to 99% (as determined by HPLC).

A crystalline salt of this invention may be prepared by contacting biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester with about 0.75 to about 1.3 molar equivalents of succinic acid. Generally, this reaction is conducted in an inert diluent at a temperature ranging from about 0° C. to about 60° C.; including about 20° C. to about 55° C., such as about 25° C. to about 55° C. Suitable inert diluents for this reaction include, but are not limited to, methanol, ethanol, isopropanol, isobutanol, ethyl acetate, tetrahydrofuran, dichloromethane and the like, or a mixture thereof, optionally containing water.

In one embodiment, the succinic acid may be added as a solution, in a solvent such as ethanol or isopropanol, to a solution of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester. The solution of the thus formed salt is then allowed to cool over a period of time, optionally with seeding at an intermediate temperature, and optionally with stirring, to allow crystalline product to form.

In a further embodiment, a solution of succinic acid in ethanol is added to a solution of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester in a similar volume of tetrahydrofuran, at a temperature of about 55° C., this solution is then cooled to about 45° C., seeded, then further cooled to about 20° C. and left stirring over an extended period, for instance about 48 h, as crystalline product is formed.

In a further embodiment, a solution of succinic acid in isopropanol may be added to a solution of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester in about three times the volume of tetrahydrofuran, at a temperature of about 37° C., this solution is then seeded and then held at this temperature for about four hours, then further cooled to about 15° C. over a period of several hours, for example about 4 hours, and then left at this temperature, as crystalline product is formed. This process was found to provide predominantly Form 3.

In a further embodiment, a crystalline succinic acid salt may be prepared from the compound of formula I by adding a solution of succinic acid in ethanol portionwise to a solution of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester in ethanol, at a temperature of about 50° C., over a period of about 4 h, followed by the addition of water (about 10 to 15% by volume, and then temperature cycling for instance over the range 0 to 40° C., over a period of several days, for instance 2 to 5 days, typically about 3 days. This process was found to provide predominantly Form 1.

In a further embodiment, a crystalline succinic acid salt may be prepared from the compound of formula I by adding a solution of succinic acid portionwise over a period of hours, for instance 3 to 7 h, typically about 5 h, to a suspension of the compound of formula I in an inert liquid such as methanol or tetrahydrofuran, at an elevated temperature, for instance in the range 40 to 60° C., typically about 50° C., and then subjecting the resultant slurry to temperature cycling, for instance over the range 0 to 40° C., over a period of several days, for instance 3 to 7 days, typically about 5 days. This process was found to provide predominantly Form 2 (solvent=methanol) or predominantly Form 3 (solvent=THF), depending on the solvent used.

In the foregoing processes, the product from the deprotection of the silyl-protected derivative of the compound of formula I may be contacted with succinic acid without the need for full isolation or purification of the intermediate product.

It will be appreciated that the purity of the initially prepared crystalline salt may be improved by recrystallisation. Furthermore, recrystallisation conditions may be selected which determine which Form of the salt is obtained.

Thus, it has been found that Form 1 may be conveniently prepared by anti-solvent recrystallisation of initially prepared crystalline salt from aqueous THF using a lower alcohol such as ethanol or isopropanol as anti-solvent. The % of water is found to be important, as too little results in incomplete dissolution whilst too much leads to incomplete recrystallisation to occur slowly, over a period of hours, to improve the quality of the crystals thus formed. In contrast, the solubility characteristics and difference in solubility between higher and lower temperatures in a range of single solvents appeared to preclude solvent recrystallisation.

Accordingly, in a further embodiment, the present invention provides a process for preparing the Form 1 succinate salt which process comprises the steps:
dissolving the succinate salt in aqueous THF (10-18%, for example 10-16%), at a temperature in the range 18 to 23° C., for example about 20° C.;
adding a first volume of a lower alcohol as an antisolvent, for example ethanol or isopropanol, in particular isopropanol, and warming to 32-40° C., typically 36±3° C.;
optionally seeding with Form 1;
adding a second volume of the lower alcohol, for example over several hours, preferably about 12 h;
cooling to a temperature in the range 18 to 23° C., for example about 20° C.; and
collecting the crystalline product.

In particular embodiment, a crystalline succinic acid salt, for example the Form 3 salt, is dissolved in tetrahydrofuran containing 14% water, at a temperature of about 20° C. to which a similar volume of isopropanol may then be added.

The solution is warmed to about 36° C., and seed crystals then added. Typically, the ratio of the weight of seed crystals to the weight of crystalline salt in the solution is about 1:400. The solution is then stirred at this temperature for a short time, for example about 1 hour, after which further isopropanol is added over a period of hours, for example about 12 hours, during which time crystallization occurs. After a further short period, for example about 1 hour, the thus formed suspension is cooled to a temperature of about 20° C. and left for a further short period, for example 1 hour, before crystalline product, for instance the Form 1 salt, is collected by filtration.

It has been found useful to prepare the crystalline succinic acid salt with a level of purity suitable for use as an active pharmaceutical ingredient (API) by a two step process, involving the initial preparation of an intermediate grade of the salt, followed by the recrystallisation of this intermediate grade product, in a controlled manner and with seeding, to obtain the desired Form, having the desired crystal quality. In one embodiment, the intermediate grade is isolated as essentially the Form 3, as a consequence of the conditions used, and this is then converted to the desired Form 1 form by anti-solvent recrystallisation.

High throughput polymorph screening techniques, by variation in crystallization conditions, for instance, solvent, temperature, are now being developed and becoming available to the skilled man or being offered by commercial suppliers such as Avantium Technologies. Further crystalline solid state forms may be identified using such high through put techniques.

In a further aspect of the present invention, it has been found that a grade of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester suitable for use in a subsequent succinic acid salt forming reaction (so-called Intermediate Grade compound, the initial product of stage 3) may be conveniently prepared from 1-(3-{[2-chloro-4-(hydroxymethyl)-5-methoxyphenyl]amino}-3-oxopropyl)piperidin-4-yl biphenyl-2-ylcarbamate (International Patent application no PCT/US2004/00449, publication no. WO 2004/074246 A2, at page 134, Preparation 96) in a three step process, without the need for full isolation and purification of the intermediates, from stages 1 and 2, according to scheme 1:

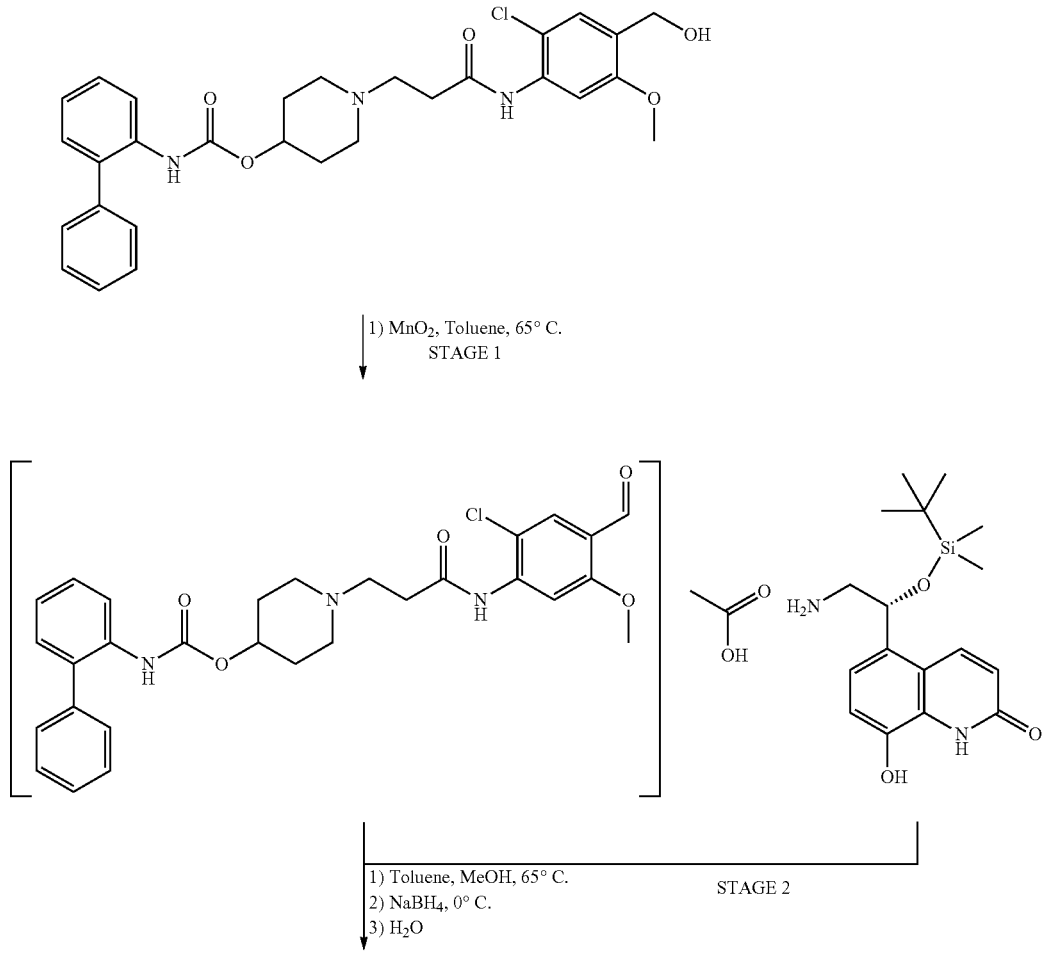

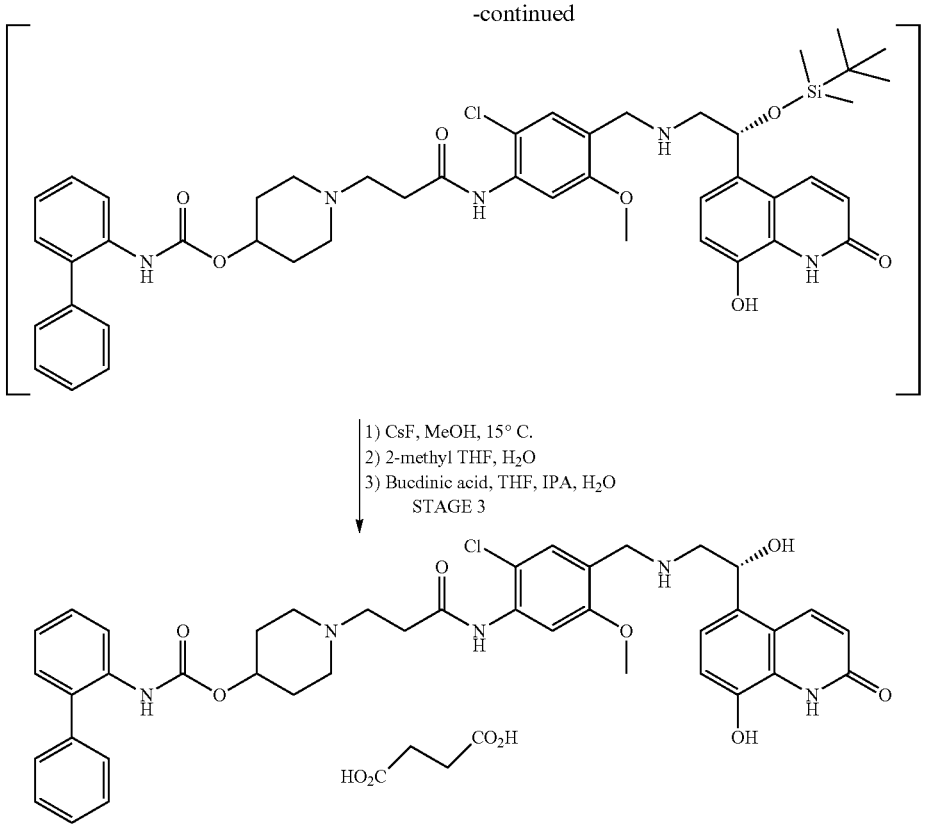

Solid State Forms

In a further embodiment, the present invention provides three distinct crystalline solid state forms of the succinic acid salt of biphenyl-2-ylcarbamic acid 1-[2-(2-chloro-4-{[(R)-2-hydroxy-2-(8-hydroxy-2-oxo-1,2-dihydroquinolin-5-yl) ethylamino]methyl}-5-methoxyphenylcarbamoyl)ethyl]piperidin-4-yl ester, forms 1, 2 and 3, that have been identified by differential scanning calorimetry (DSC). The preferred solid state form, designated as Form 1, is characterized by a high melting point, as evidenced by a differential scanning calorimetry (DSC) trace, at about 174° C. The remaining solid state forms, Forms 2 and 3, are characterized by melting points, as evidenced by differential scanning calorimetry (DSC) traces, at about 161° C. and 150° C. respectively.

Furthermore, Form 1 is characterized by an x-ray powder diffraction (XRPD) pattern having significant diffraction peaks at 2θ values of 5.0±0.3, and 10.0±0.3.

Furthermore, Form 2 is characterized by an x-ray powder diffraction (XRPD) pattern having significant diffraction peaks at 2θ values of 5.0±0.3, and 9.9±0.3.

Furthermore, Form 3 is characterized by an x-ray powder diffraction (XRPD) pattern having a significant diffraction peaks at 2θ values of 5.0±0.3.

In addition, Form 1 is characterized by its infrared (IR) absorption spectrum which shows significant absorption bands at about: 3265, 2832, 1735, 1718, 1679, 1669, 1591, 1540, 1518, 1493, 1439, 1405, 1339, 1302, 1283, 1239, 1202, 1163, 1144, 1107, 1095, 1039, 1009, 973, 921, 885, 868, 838, 773, 751, and 707 cm$^{-1}$.

In addition, Form 2 is characterized by its infrared (IR) absorption spectrum which shows significant absorption bands at about: 3317, 2947, 1728, 1678, 1667, 1591, 1537, 1494, 1453, 1439, 1403, 1339, 1302, 1284, 1213, 1172, 1111, 1058, 1046, 999, 975, 885, 839, and 750 cm$^{-1}$.

In addition, Form 3 is characterized by its infrared (IR) absorption spectrum which shows significant absorption bands at about: 3335, 2949, 1745, 1715, 1678, 1641, 1592, 1542, 1493, 1464, 1439, 1405, 1338, 1303, 1283, 1247, 1211, 1170, 1109, 1093, 1053, 1041, 997, 974, 919, 889, 842, 774, 766, 751 and 721 cm$^{-1}$.

Form 1 has been demonstrated to have a reversible sorption/desorption profile with a good level of hygroscopicity (i.e. less than about 2.0% weight gain in the humidity range of 30% relative humidity to 90% relative humidity), as shown by its Dynamic Vapour Sorption profile.

These properties of the salts of this invention are further illustrated in the Examples below.

Pharmaceutical Compositions and Formulations

The succinic acid salt of the compound of formula I may typically be administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration, in particular inhaled administration. However, it will be understood by those skilled in the art that, once the crystalline salt of this invention has been formulated, it may no longer be in a crystalline form, i.e., the salt may be dissolved in a suitable carrier, or the original crystalline form.

Accordingly, in one of its compositions aspects, this invention is directed to a pharmaceutical composition comprising a pharmaceutically acceptable carrier or excipient and a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbomyl) ethyl]piperidin-4-yl ester or a solvate thereof. Optionally, such pharmaceutical compositions may contain other therapeutic and/or formulating agents if desired.

The pharmaceutical compositions of this invention typically contain a therapeutically effective amount of a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbomyl)ethyl] piperidin-4-yl ester or a solvate thereof. Typically, such pharmaceutical compositions will contain from about 0.1 to about 95% by weight of the active agent; including, from about 0.01 to about 30% by weight; such as from about 0.01 to about 10% by weight of the active agent.

Any conventional carrier or excipient may be used in the pharmaceutical compositions of this invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in *Remington: The Science and Practice of Pharmacy*, $20^{th}$ Edition, Lippincott Williams & White, Baltimore, Md. (2000); and H. C. Ansel et al., *Pharmaceutical Dosage Forms and Drug Delivery Systems*, $7^{th}$ Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

The pharmaceutical compositions of this invention are typically prepared by thoroughly and intimately mixing or blending a salt of the invention with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of this invention are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a specific embodiment of this invention, the pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Suitable nebulizer devices are provided commercially, for example, by PARI GmbH (Starnber, German). Other nebulizer devices include Respimat (Boehringer Ingelheim) and those disclosed, for example, in U.S. Pat. No. 6,123,068 and WO 97/12687.

A representative pharmaceutical composition for use in a nebulizer inhaler comprises an aqueous solution comprising from about 0.05 μg/mL to about 10 mg/mL of a succinic acid salt of compound of formula I or a solvate thereof. In one embodiment, the aqueous nebulizer formulation is isotonic. In one embodiment, the aqueous nebulizer formulation has a pH in the range of from about 4 to about 6. In a particular embodiment, the aqueous nebulizer formulation is buffered with citrate buffer to a pH of about 5. In another particular embodiment, the aqueous nebulizer formulation contains from about 0.1 mg/mL to about 1.0 mg/mL free base equivalents of biphenyl-2-ylcarbamic acid 1-[2-(2-chloro-4-{[(R)-2-hydroxy-2-(8-hydroxy-2-oxo-1,2-dihydroquinolin-5-yl) ethylamino]methyl}-5-methoxyphenylcarbamoyl)ethyl] piperidin-4-yl ester.

In another specific embodiment of this invention, the pharmaceutical composition comprising the active agent is administered by inhalation using a dry powder inhaler. Such dry powder inhalers typically administer the active agent as a free-flowing powder that is dispersed in a patient's air-stream during inspiration. In order to achieve a free flowing powder, the active agent is typically formulated with a suitable excipient such as lactose, starch, mannitol, dextrose, polylactic acid (PLA), polylactide-co-glycolide (PLGA) or combinations thereof. Typically, the active agent is micronized and combined with a suitable carrier to form a blend of micronized particles of respirable size, where "micronized particles" or "micronized form" means at least about 90% of the particles have a diameter of less than about 10 μm. The dry powder composition may further comprise a ternary agent such as magnesium stearate, presenting from 0.1-2% w/w, to stabilize the composition.

A representative pharmaceutical composition for use in a dry powder inhaler comprises lactose having a particle size between about 1 μm and about 100 μm and micronized particles of a succinic acid salt of compound of formula I, or a solvate thereof.

Such a dry powder composition can be made, for example, by combining the lactose with the active agent and then dry blending the components. Alternatively, if desired, the active agent can be formulated without an excipient. The pharmaceutical composition is then typically loaded into a dry powder dispenser, or into inhalation blister strips, cartridges or capsules for use with a dry powder delivery device. Examples of dry powder inhaler delivery devices include Diskhaler (GlaxoSmithKline, Research Triangle Part, N.C.) (see, e.g., U.S. Pat. No. 5,035,237); Diskus (GlaxoSmithKline) (see, e.g., U.S. Pat. No. 6,738,519; Turbuhaler (AstraZeneca, Wilmington, Del.) (see e.g., U.S. Pat. No. 4,524,769); Rotahaler (GlaxoSmithKline) (see, e.g., U.S. Pat. No. 4,353, 365) and Handihaler (Boehringer Ingelheim). Further examples of suitable DPI devices are described in U.S. Pat. Nos. 5,415,162, 5,239,993, and 5,715,810, WO-A-2006/ 018261, and WO-A-03/061743, and references cited therein.

In yet another specific embodiment of this invention, the pharmaceutical composition comprising the active agent is administered by inhalation using a metered-dose inhaler. Such metered-dose inhalers typically discharge a measured amount of the active agent or a pharmaceutically acceptable salt thereof using compressed propellant gas. Accordingly, pharmaceutical compositions administered using a metered-dose inhaler typically comprise a solution or suspension of the active agent in a liquefied propellant. Any suitable liquefied propellant may be employed including chlorofluorocarbons, such as $CCl_3F$, and hydrofluoroalkanes (HFAs), such as 1,1,1,2-tetrafluorethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents, such as ethanol or pentane, and surfactants, such as a sorbitan trioleate, oleic acid, lecithin, and glycerin. See, for example, U.S. Pat. No. 5,225,183, EP 0717987 A2, and WO 92/22286.

A representative pharmaceutical composition for use in a metered-dose inhaler comprises from about 0.01% to about 5% by weight of a succinic acid salt of compound of formula I, or a solvate thereof; from about 0% to about 20% by weight ethanol; and from about 0% to about 5% by weight surfactant; with the remainder being an HFA propellant.

Such compositions are typically prepared by adding chilled or pressurized hydrofluroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of metered-dose inhaler devices developed specifically for use with HFA propellants are provided in U.S. Pat. Nos. 6,006,745 and 6,143,277. Alternatively, a suspension formulation can be prepared by spray drying a coating of surfactant on micronized particles of the active agent. See, for example, WO 99/53901 and WO 00/61108.

For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

The pharmaceutical compositions of this invention may also contain other therapeutic agents that are co-administered with a succinic acid salt of compound of formula I or solvate thereof. For example, the pharmaceutical compositions of this invention may further comprise one or more therapeutic agents selected from anti-inflammatory agents (e.g. steroidal anti-inflammatory agents, such as corticosteroids; and non-steroidal anti-inflammatory agents (NSAIDs), phosphodiesterase IV inhibitors, anti-infective agents (e.g. antibiotics or antivirals), antihistamines, $\beta_3$ adrenergic receptor agonists, muscarinic receptor antagonist (i.e., anticholinergic agents) and the like, in particular a steroidal anti-inflammatory agent or a muscarinic receptor antagonist. The other therapeutic agents can be used in the form of pharmaceutically acceptable salts or solvates. Additionally, if appropriate, the other therapeutic agents can be used as optically pure stereoisomers.

If desired, the salts of this invention can also be administered in combination with another therapeutic agent or agents, such those described herein. In this embodiment, the components are not physically mixed together but are administered simultaneously or sequentially as separate compositions. For example, a salt of this invention can be administered by inhalation simultaneously or sequentially with a steroidal anti-inflammatory agent, such as a corticosteroid, using an inhalation delivery device that employs separate compartments (e.g. blister packs) for each therapeutic agent. Alternatively, the combination may be administered from multiple delivery devices, i.e., one delivery device for each therapeutic agent.

Representative steroidal anti-inflammatory agents that can be used with the compounds of this invention include, but are not limited to, methyl prednisolone, prednisolone, dexamethasone, fluticasone propionate, 6,9-difluoro-17-[(2-furanylcarbonyl)oxy]-11-hydroxy-16-methyl-3-oxoandrosta-1,4-diene-17-carbothioic acid S-fluoromethyl ester, 6,9-difluoro-11-hydroxy-16-methyl-3-oxo-17-propionyloxy-androsta-1,4-diene-17-carbothioic acid S-(2-oxotetrahydrofuran-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, ST-126 and the like, or pharmaceutically-acceptable salts thereof. In a particular embodiment, the steroidal anti-inflammatory agent is 6α,9α-difluoro-17α-[(2-furanylcarbonyl)oxy]-11β-hydroxy-16α-methyl-3-oxoandrosta-1,4-diene-17β-carbothioic acid S-fluoromethyl ester or a pharmaceutically acceptable salt or solvate thereof. When employed, the steroidal anti-inflammatory agent will be present in the pharmaceutical composition in a therapeutically effective amount. Typically, the steroidal anti-inflammatory agent will be present in an amount sufficient to provide from about 0.05 µg to about 500 µg per dose.

Representative muscarinic antagonists (i.e., anticholinergic agents) that can be used with the compounds of this invention include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anistropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; for those compounds listed as a salt, alternate pharmaceutically acceptable salt thereof.

Representative antihistamines, phosphodiesterase-4 (PDE4) inhibitors or mixed PDE3/PDE4 inhibitors and $\beta_2$ adrenergic receptor agonists that can be used with the compounds of this invention are described in International Patent application no PCT/US2004/004449, publication no. WO 2004/074246 A2.

Other therapeutic agents which may be used with compounds of the present invention include, for example, other anti-inflammatory agents, e.g., NSAIDs (such as sodium chromoglycate; nedocromil sodium; leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (IL antibody), specifically, an IL-4 therapy, an IL-13 therapy, or a combination thereof); or inhibitors of cytokine synthesis. Suitable doses for the other therapeutic agents administered with a compound of the invention are in the range of about 0.05 mg/day to about 100 mg/day.

The following formulations illustrate representative pharmaceutical compositions of the present invention:

Formulation Example A

A dry powder for administration by inhalation is prepared as follows:

| Ingredients | Amount |
|---|---|
| Salt of the invention | 0.2 mg |
| Lactose | 25 mg |

Representative Procedure: The compound of the invention is micronized and then blended with lactose. This blended mixture is then loaded into a gelatin inhalation cartridge. The contents of the cartridge are administered using a powder inhaler.

Formulation Example B

A dry powder formulation for use in a dry powder inhalation device is prepared as follows:

Representative Procedure: A pharmaceutical composition is prepared having a bulk formulation ratio of micronized salt of the invention to lactose of 1:200. The composition is packed into a dry powder inhalation device capable of delivering between about 10 μg and about 100 μg of the compound of the invention per dose.

Formulation Example C

A dry powder for administration by inhalation in a metered dose inhaler is prepared as follows:

Representative Procedure: A suspension containing 5 wt % of a salt of the invention and 0.1 w. % lecithin is prepared by dispersing 10 g of the compound of the invention as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

Formulation Example D

A pharmaceutical composition for use in a metered dose inhaler is prepared as follows:

Representative Procedure: A suspension containing 5% salt of the invention, 0.5% lecithin, and 0.5% trehalose is prepared by dispersing 5 g of active ingredient as micronized particles with mean size less than 10 m in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

Formulation Example E

A pharmaceutical composition for use in a nebulizer inhaler is prepared as follows:

Representative Procedure: An aqueous aerosol formulation for use in a nebulizer is prepared by dissolving 0.5 mg of the salt of the invention in 1 mL of a 0.9% sodium chloride solution acidified with citric acid. The mixture is stirred and sonicated until the active ingredient is dissolved. The pH of the solution is adjusted to a value of about 5 by the slow addition of NaOH.

Formulation Example F

Bulk formulations were prepared comprising 0.8%, 1.6% and 4% w/w of succinate salt (Form 1, micronised to give a median size of approx 2 microns) in lactose monohydrate (having a mass median size of 70-90 microns), to provide 100, 200 and 500 μg of free base (Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester) per blister, for use in DISKUS™ dry powder inhalation device.

Formulations as above were also prepared but also comprising magnesium stearate as a stabiliser, at levels from 0.2-1% w/w.

Utility

The compound of formula I possesses both $\beta_2$ adrenergic receptor agonist and muscarinic receptor antagonist activity and, therefore, a succinic acid salt of the compound of formula I of the present invention is expected to be useful as a therapeutic agent for treating medical conditions mediated by $\beta_2$ adrenergic receptors or muscarinic receptors, i.e., medical conditions that are ameliorated by treatment with a $\beta_2$ adrenergic receptor agonist or a muscarinic receptor antagonist. Such medical conditions include, by way of example, pulmonary disorders or diseases including those associated with reversible airway obstruction, such as chronic obstructive pulmonary disease (e.g., chronic and wheezy bronchitis and emphysema), asthma, pulmonary fibrosis, allergic rhinitis, rhinorrhea, and the like. Other conditions which may be treated include premature labor, depression, congestive heart failure, skin diseases (e.g., inflammatory, allergic, psoriatic and proliferative skin diseases, conditions where lowering peptic acidity is desirable (e.g., peptic and gastric ulceration) and muscle wasting disease.

Accordingly, in one embodiment, this invention is directed to a method for treating a pulmonary disorder, the method comprising administering to a patient in need of treatment a therapeutically effective amount of a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof. When used to treat a pulmonary disorder, the salt of this invention will typically be administered by inhalation in multiple doses per day, in a single daily dose or a single weekly dose. Generally, the dose for treating a pulmonary disorder will range from about 10 μg/day to about 200 μg/day.

When administered by inhalation, the compounds of this invention typically have the effect of providing bronchodilation. Accordingly, in another of its method aspects, this invention is directed to a method of providing bronchodilation in a patient in need of bronchodilation, the method comprising administering to the patient a bronchodilation-producing amount of a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester or a solvate thereof. Generally, the dose for providing bronchodilation will range from about 10 μg/day to about 200 μg/day.

In one embodiment, this invention is directed to a method of treating chronic obstructive pulmonary disease or asthma, the method comprising administering to a patient in need of treatment a therapeutically effective amount of a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl) ethyl]-piperidin-4-yl ester or a solvate thereof. When used to treat a COPD or asthma, the salt of this invention will typically be administered by inhalation in multiple doses per day or in a single daily dose. Generally, the dose for treating COPD or asthma will range from about 10 µg/day to about 200 µg/day. As used herein, COPD includes chronic obstructive bronchitis and emphysema (see, for example, Barnes, Chronic Obstructive Pulmonary Disease, *N Engl J Med* 2000: 343:269-78).

When used to treat a pulmonary disorder, the salt of this invention is optionally administered in combination with other therapeutic agents. Accordingly, in a particular embodiment, the pharmaceutical compositions and methods of this invention further comprise a therapeutically effective amount of a steroidal anti-inflammatory agent. The properties and utility of succinic acid salts of this invention can be demonstrated using various in vitro and in vivo assays well-known to those skilled in the art. For example, representative assays are described in International Patent application no PCT/US2004/004449, publication no. WO 2004/074246 A2 (Theravance Inc, South San Francisco, Calif., US).

EXAMPLES

The following Preparations and Examples are provided to illustrate specific embodiments of this invention. These specific embodiments, however, are not intended to limit the scope of this invention in any way unless specifically indicated.

Unless noted otherwise, reagents, starting materials and solvents were purchased from commercial suppliers (such as Sigma-Aldrich, Fluka and the like) and were used without further purification.

1-(3-{[2-chloro-4-(hydroxymethyl)-5-methoxyphenyl] amino}-3-oxopropyl)piperidin-4-yl biphenyl-2-ylcarbamate may be prepared according to the description provided in International Patent application no PCT/US2004/004449, publication no. WO 2004/074246 A2, at page 134, Preparation 96.

Biphenyl-2-ylcarbamic Acid 1-[2-(4-{[(R)-2-(tert-Butyldimethylsilanyloxy)-2-(8-hydroxy-2-oxo-1,2-dihydroquinolin-5-yl)ethylamino]methyl}-2-chloro-5-methoxyphenylcarbamoyl)-ethyl]piperidin-4-yl Ester may be prepared according to the description provided in International Patent application No PCT/US2004/004449, publication no. WO 2004/074246 A2, at page 135, Preparation 98.

Example 1

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester Succinic Acid Salt 1-(3-{[2-chloro-4-(hydroxymethyl)-5-methoxyphenyl] amino}-3-oxopropyl)piperidin-4-yl biphenyl-2-ylcarbamate (69 g) was suspended in toluene (480 mL) at ~65° C. Manganese dioxide (48 g) was added and the resulting mixture stirred at ~65° C. for about 6 hours. The mixture was then diluted with toluene (300 mL), and Celite (24 g) added. The resulting mixture was filtered and washed with toluene (180 ml), to remove manganese residues. The resulting solution was concentrated to about half the original volume (540 ml), cooled to ~20° C., and diluted with methanol (240 mL). 5-((1R)-2-amino-1-{[tert-butyl (dimethyl)silyl]oxy}ethyl)-8-hydroxyquinolin-2(1H)-one acetate (48.4 g) was added and the mixture stirred at ~65° C. until dissolution was complete. The solution was cooled to ~−2° C. and sodium borohydride (2.12 g) was added in 4 portions over 1 h. Upon complete addition the reaction was quenched by the addition of water (300 mL). The mixture was stirred thoroughly and then the layers were separated, at ~20° C. Methanol (540 mL) was added to the organic layer and this was then concentrated to about a third of the original volume. Additional methanol (600 mL) was added to the residue which was then concentrated to about half the original volume. The solution was cooled to ~17° C. and cesium fluoride (54.1 g) and acetic acid (9.2 g) were added. The resulting mixture was stirred at ~17° C. for about 13 hours. Upon complete reaction, 2-methyltetrahydrofuran (605 mL) and water (275 mL) were added. The mixture was stirred thoroughly and the layers then separated. The organic layer was washed with aqueous saturated sodium hydrogen carbonate solution (275 mL) and then water (220 mL). The organic layer was then concentrated to about half the original volume by vacuum distillation before being diluted with THF (500 mL)*. The solution was warmed to ~37° C. and a solution of succinic acid (11.0 g) in isopropanol (250 ml) was added. The solution was then seeded (with Form 1), held at ~37° C. for about 4 hours, cooled to ~15° C. over about 4 hours before being held at ~15° C. for 84 hours. The resulting solid was isolated by filtration, washed with THF:isopropanol:water mixture (50:50:3, 300 mL) and TBME (300 mL) before being dried in vacuo at ~45° C. to provide the title compound as a white powder which was almost exclusively (~98%) Form 3 (55.0 g).

* the organic layer may be evaporated to dryness to provide biphenyl-2-ylcarbamic acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl ester, for subsequent conversion to succinate salt.

1H NMR (500 MHz, DMSO-d6): δ(ppm): 10.27 (s, 1H), 8.67 (s, 1H), 8.11 (d, 1H, J=9.5), 7.79 (s, 1H), 7.33 (m, 10H), 7.07 (d, 1H, J=8.0), 6.93 (d, 1H, J=8.5), 6.49 (d, 1H, J=10.0), 5.10 (m, 1H), 4.50 (m, 1H), 3.80 (s, 2H), 3.73 (s, 3H), 2.74 (m, 4H), 2.62 (m, 2H), 2.55 (m, 2H), 2.38 (s, 4H), 2.24 (m, 2H), 1.77 (m, 2H), 1.51 (m, 2H); m/z: [M+H+] calculated for C40H42ClN5O7, 740.29; found 740.24

Preparation 1

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester 1-(3-{[2-chloro-4-(hydroxymethyl)-5-methoxyphenyl] amino}-3-oxopropyl)piperidin-4-yl biphenyl-2-ylcarbamate (12.5 g) and manganese dioxide (8 g) were heated together in toluene (94 mL) at ~60° C. for 5 h. The manganese dioxide (8 g) was then removed by filtration through Celite (2 g), with washing with toluene (2×3 ml). The resulting solution was concentrated (to about 100 ml) and then warmed to ~60° C. 5((1R)-2-amino-1-{[tert-butyl(dimethyl)silyl]oxy}ethyl)-8-hydroxyquinolin-2(1H)-one acetate (8 g) and methanol (19 ml) were added and the mixture stirred until dissolution was complete. The solution was cooled to ~−5° C., sodium borohydride (0.28 g) was added and the mixture then stirred for 2 h. Water (50 ml) was then added, to quench the reaction and the mixture stirred vigorously at 20° C. for 30 min. The layers were separated and the aqueous discarded. The organic layer was then solvent switched into methanol (75 ml). Cesium fluoride (11.4 g) and acetic acid (1.7 g) were added and the resulting mixture was stirred at 20° C. for about 22 hours. The mixture was reduced in volume (to approximately 60 ml) and methyltetrahydrofuran (100 ml) and water (50 ml) added, to enable a phase separation. The aqueous layer was discarded and the organic layer evaporated to dryness to provide the title compound as a solid (12.0 g. 70%).

Example 2

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester Succinic Acid Salt (Form 1)

Ethanol (14 ml) was added to Biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl ester (1.5 g) and heated at ~70° C. for 1 h. The temperature was then lowered to 50° C. and succinic acid (251.25 mg, 1.05 equiv) in ethanol (2 ml) was added portionwise over approximately 4 hours. After all the acid was added, water (2.25 ml) was added, followed by a further 30 min at 50° C. The reaction was then temperature cycled between 0° C. and 40° C. over 3 days. The resulting white solid was isolated by filtration, washed with ethanol and dried in a vacuum oven at ambient temperature, to provide the title compound as a crystalline solid (727 mg).

Example 3

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester Succinic Acid Salt (Form 2)

Biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl ester (prepared as in Preparation 1) (200 mg) was suspended in methanol (1.5 ml) at ~70° C. A first portion (100 μl) of succinic acid in methanol was added, from a total of succinic acid (67 mg, 2.1 equiv) in methanol (0.5 ml), and the temperature reduced to 50° C. The remaining succinic acid in methanol was added in four further portions (100 μl) over approximately 5 hours, with further methanol (1 ml) added after 3 h, to replace lost solvent. After a further 30 min. The resulting slurry was temperature cycled between 0° C. and 40° C. over 5 days. The resulting solid was isolated by filtration, washed with THF, dried on filter paper and then in a vacuum oven, to provide the title compound as a crystalline solid (148 mg).

Example 4

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester Succinic Acid Salt (Form 2)

Biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl ester (2 g) was dissolved in methanol (16 ml) at ~70° C., over a period of 1 h. After a further 1 h, succinic acid (335 mg) in methanol (4 ml) was added and this was left to temperature cycle between 0° C. and 40° C. over 2 days. The resulting solid was isolated by filtration, washed with methanol, dried on filter paper and then dried at 40° C. in a vacuum oven overnight, to provide the title compound as a crystalline solid (979 mg). This was confirmed by DSC to be Form 2.

Example 5

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl Ester Succinic Acid Salt (Form 3)

Biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl ester (200 mg) was suspended in tetrahydrofuran (1.5 ml) at ~70° C. A first portion (100 μl) of succinic acid in methanol was added, from a total of succinic acid (33.5 mg, 1.05 equiv) in THF (0.5 ml) and the temperature reduced to 50° C. The remaining succinic acid in methanol was added in four further portions over approximately 5 hours, with further THF (1 ml) added after 1 h, to replace lost solvent. After a further 30 min, the resulting slurry was temperature cycled between 0° C. and 40° C. over 5 days. The resulting solid was isolated by filtration, washed with methanol, dried on filter paper overnight and then in a vacuum oven, to provide the title compound as a crystalline solid (140 mg).

Example 6

Biphenyl-2-ylcarbamic Acid 1-[2-(2-Chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl Ester Succinic Acid Salt (Form 1)

Biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)-ethyl]piperidin-4-yl ester succinic acid salt, prepared as in Example 1 (363.6 g) was dissolved in 14% water in tetrahydrofuran (2906 mL) at ~20° C. and stirred for 1.5 hours until a solution was formed. Isopropanol (635 mL) was added to the clear solution which was then warmed to 36±3° C. Seed (0.91 g) was added and the solution was stirred at ~36±3° C. for about 1 hour. Isopropanol (6080 mL) was then added to the mixture over about 12 hours. The suspension was then held at 36±3° C. for about 1 hour before being cooled to ~20° C. and held at this temperature for at least a further hour. The resulting precipitate was isolated by filtration, washed with THF:isopropanol:water (70:25:5, 3636 mL) and then TBME (363 mL) and dried in vacuo at ~60° C. to provide the title compound as a crystalline solid.

Example 7

Thermal Analysis

DSC thermograms of the solid state forms Form 1, 2 and 3 were obtained using a TA Instruments Q1000 calorimeter number: 970001.901, and serial number: 1000-0126. The sample was weighed into an aluminum pan, a pan lid placed on top and lightly crimped without sealing the pan. The experiments were conducted using a heating rate of 10° C. min$^{-1}$.

Figure 2:
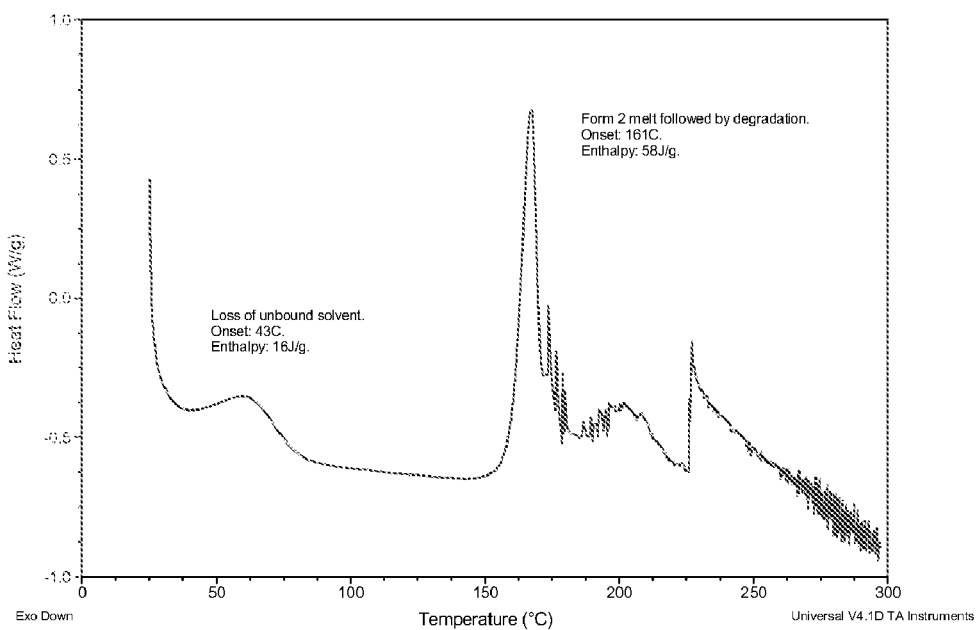
FIG. 2 shows a differential scanning calorimetry (DSC) trace for a sample of a second crystalline solid state form of a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of this invention, hereinafter referred to as Form 2.
Figure 3:
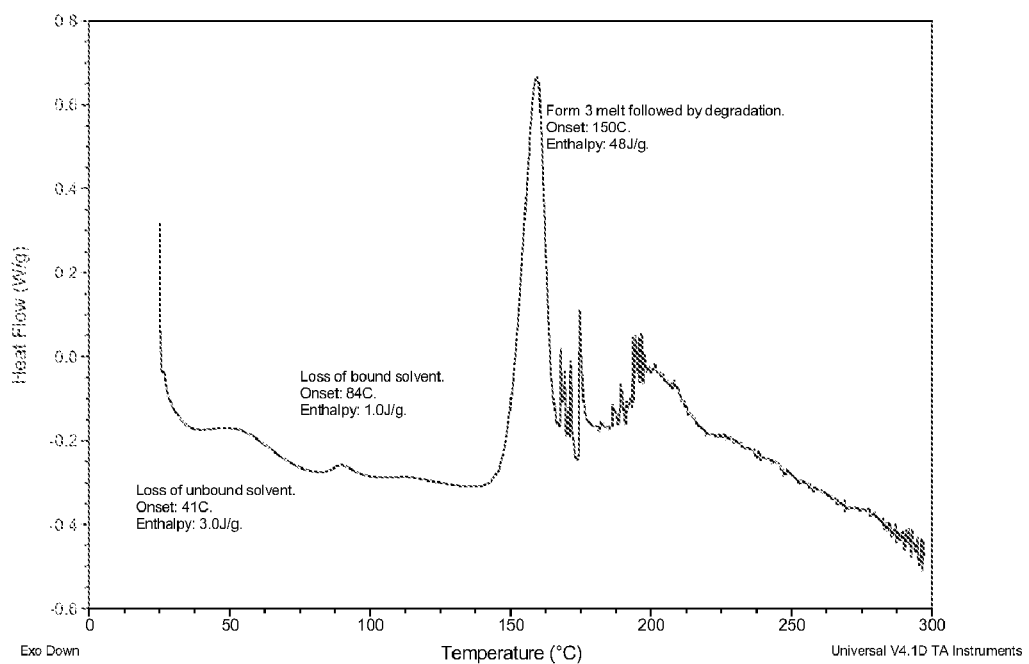
FIG. 3 shows a differential scanning calorimetry (DSC) trace for a sample of a third crystalline solid state form of a succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester of this invention, hereinafter referred to as Form 3.

A representative DSC thermogram for a sample of each of the Form 1, 2 and 3 succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, as prepared by the method described in Examples 2, 3 and 5, is shown in FIGS. 1 to 3.

Example 8—X-Ray Powder Diffraction

The X-ray powder diffraction (XRPD) data of the solid state forms Form 1, 2 and 3 were acquired on a PANalytical X.Pert Pro powder diffractomer model PW3040/60, using an XCelerator detector. The acquisition conditions were radiation: Cu Kα, generator tension 40 kV, generator current: 45 mA, start angle 2.0° 2θ, and angle 40.0° 2 θ, step size: 0.167°2θ, times per step 31.75 seconds. The sample was prepared by mounting a few milligrams of sample on a Silicon wafer (zero background) plates, resulting in a thin layer of powder. Characteristic XRPD angles and d-spacings are recorded in Table 1 for a sample of each of Forms Form 1, 2 and 3, as prepared by the method described in Examples 2, 3, and 5.

TABLE 1

Characteristic XRPD peak positions for Forms 1-3.

| Form Form 1 | | Form 2 | | Form 3 | |
|---|---|---|---|---|---|
| 2θ | d-spacing/Å | 2θ | d-spacing/Å | 2θ | d-spacing/Å |
| 5.0 | 17.7 | 5.0 | 17.8 | 5.0 | 17.6 |
| 5.7 | 15.6 | 5.7 | 15.5 | 7.2 | 12.3 |
| 7.1 | 12.4 | 7.1 | 12.4 | 11.2 | 7.9 |
| 10.0 | 8.9 | 9.0* | 9.8* | 14.3 | 6.2 |
| 12.6 | 7.0 | 9.9 | 9.0 | 15.6 | 5.7 |
| 13.8 | 6.4 | 13.8 | 6.4 | 17.4* | 5.1* |
| 14.4 | 6.1 | 14.2 | 6.2 | 20.5 | 4.3 |
| 15.5 | 5.7 | 16.6 | 5.3 | 21.5 | 4.1 |
| 16.1 | 5.5 | 17.5 | 5.1 | 25.6 | 3.5 |
| 16.4 | 5.4 | 19.7 | 4.5 | 25.9 | 3.4 |
| 16.9 | 5.3 | 20.7 | 4.3 | | |
| 17.8 | 5.0 | 21.4 | 4.2 | | |
| 18.5 | 4.8 | 25.8 | 3.4 | | |
| 20.2 | 4.4 | | | | |
| 20.5 | 4.3 | | | | |
| 21.4 | 4.1 | | | | |
| 25.3 | 3.5 | | | | |
| 25.8 | 3.5 | | | | |
| 26.3* | 3.4* | | | | |

Characteristic peak positions and calculated d-spacings are summarised in Table 1. These were calculated from the raw data using Highscore software. Peaks marked with a * distinguish that form from the others. Other peaks (underscored and in bold) also distinguish the forms, however, there are shoulders or low intensity peaks of another form in close proximity that make these peaks less specific than those with a shaded background.

Figure 4:
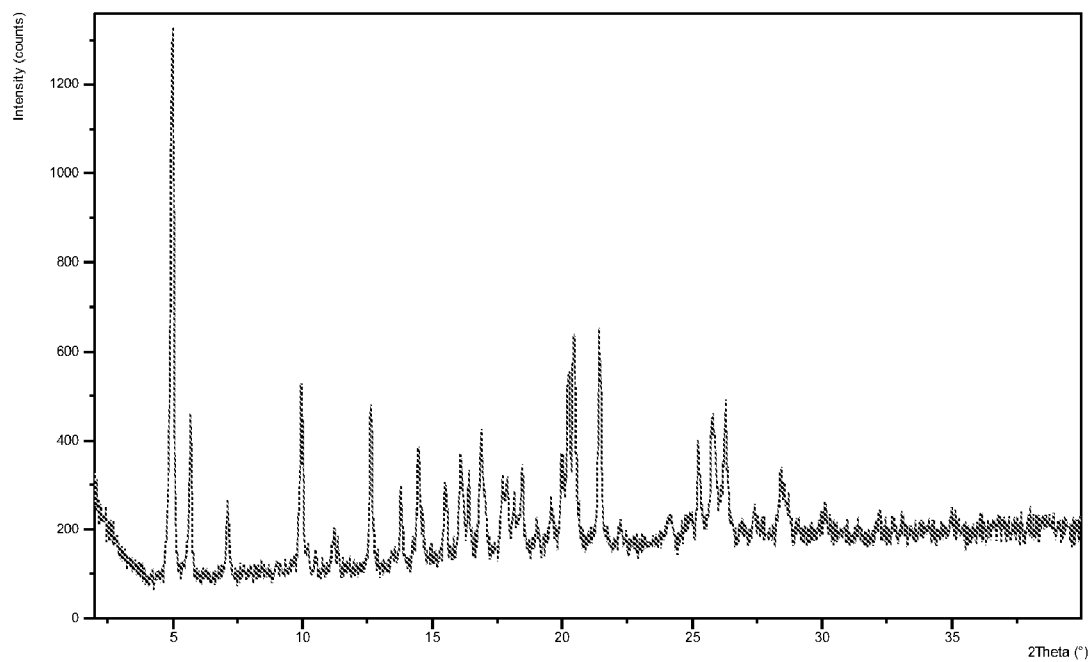
FIG. 4 shows a x-ray powder diffraction (XRPD) pattern of a sample of crystalline 1,2-succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl (Form 1).
Figure 5:
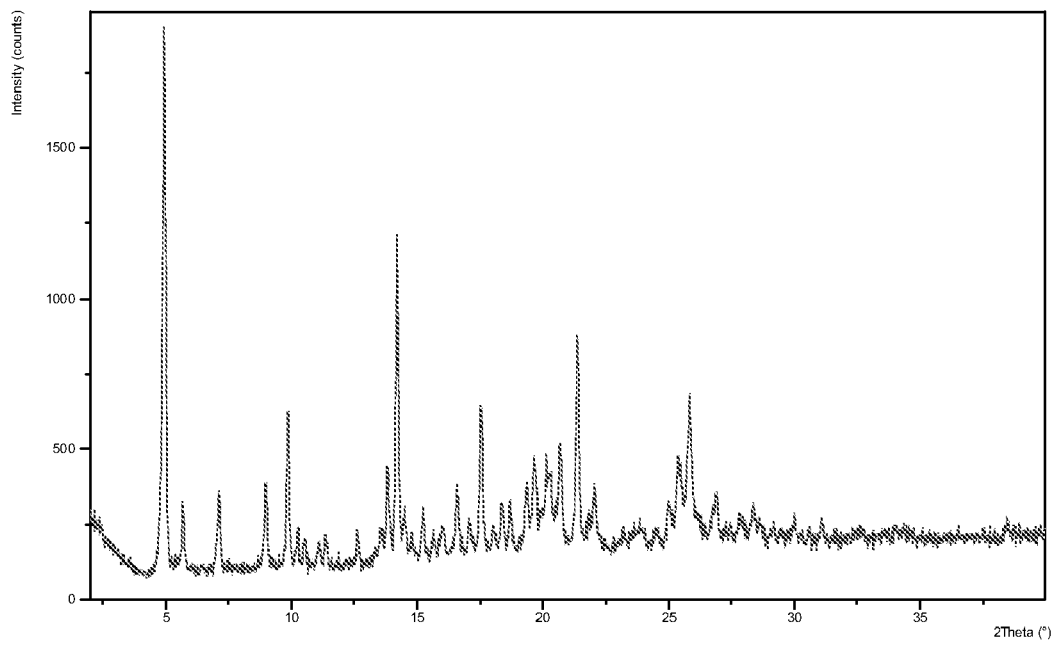
FIG. 5 shows a x-ray powder diffraction (XRPD) pattern of a sample of crystalline 1,2-succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl (Form 2).
Figure 6:
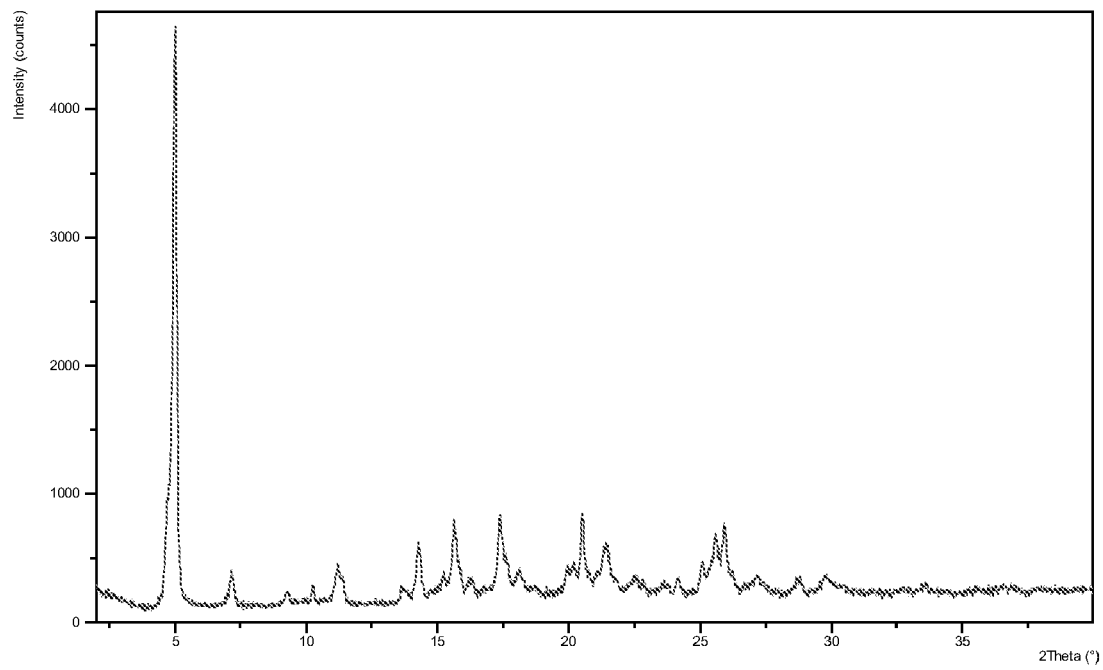
FIG. 6 shows a x-ray powder diffraction (XRPD) pattern of a sample of crystalline 1,2-succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester (Form 3).

The XRPD data are illustrated in FIGS. 4 to 6, respectively.

Example 9—FT-IR

The FT-IR spectrum of the solid forms, Forms 1, 2 and 3, was recorded using a Nicolet Avatar 360 FT-IR spectrometer, fitted with a Diamond/ZnSe ATR Accessory at 4 cm$^{-1}$ resolution, over the frequency range 4000 to 700 cm$^{-1}$.

Form 1 bands were observed at: 3265, 2832, 1735, 1718, 1679, 1669, 1591, 1540, 1518, 1493, 1439, 1405, 1339, 1302, 1283, 1239, 1202, 1163, 1144, 1107, 1095, 1039, 1009, 973, 921, 885, 868, 838, 773, 751, and 707 cm$^{-1}$.

Form 2 bands were observed at: 3317, 2947, 1728, 1678, 1667, 1591, 1537, 1494, 1453, 1439, 1403, 1339, 1302, 1284, 1213, 1172, 1111, 1058, 1046, 999, 975, 885, 839, and 750 cm$^{-1}$.

Form 3 bands were observed at: 3335, 2949, 1745, 1715, 1678, 1641, 1592, 1542, 1493, 1464, 1439, 1405, 1338, 1303, 1283, 1247, 1211, 1170, 1109, 1093, 1053, 1041, 997, 974, 919, 889, 842, 774, 766, 751 and 721 cm$^{-1}$.

Figure 7:
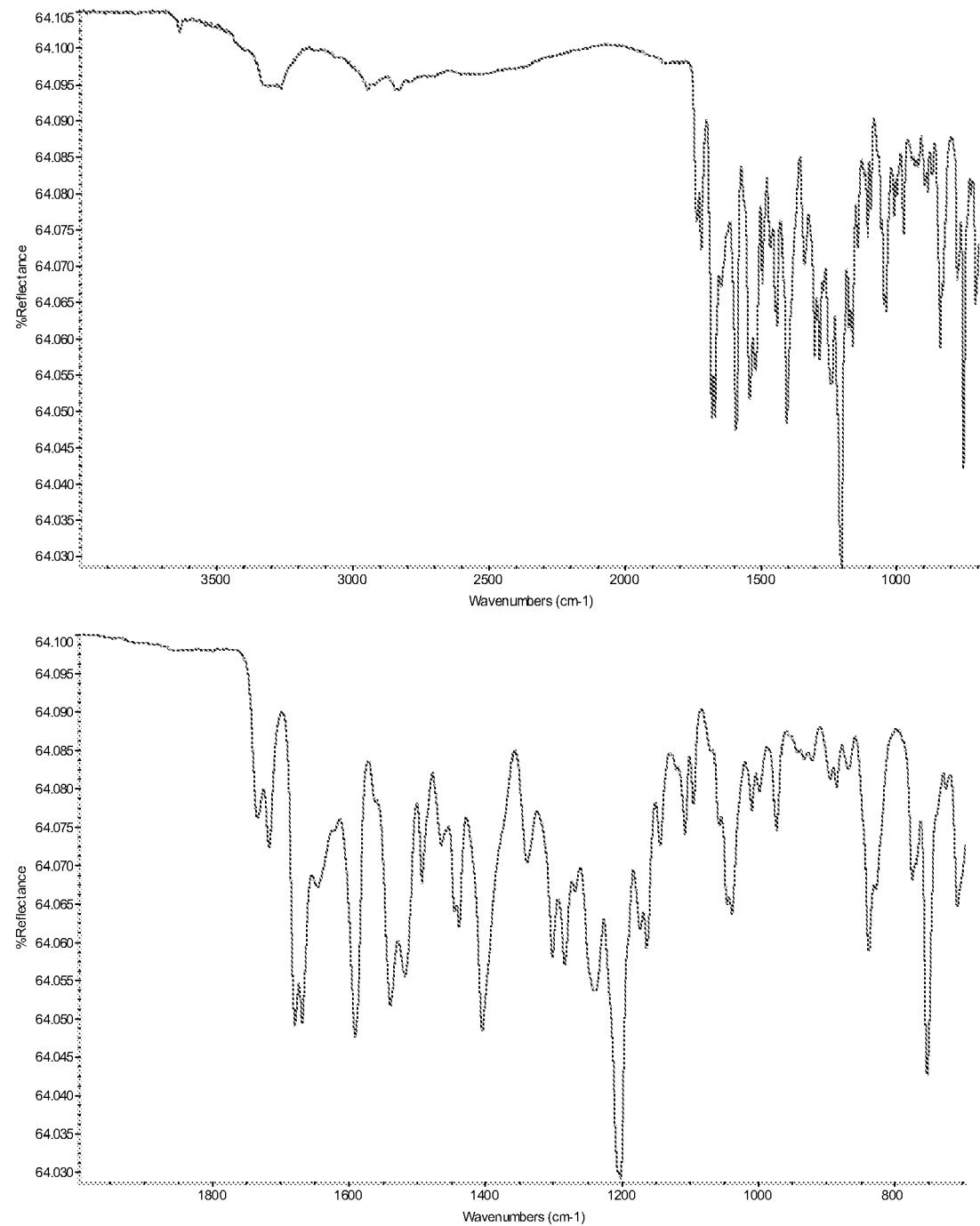
FIG. 7 shows an infrared (IR) absorption spectra of a sample of crystalline 1,2-succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester (Form 1).
Figure 8:
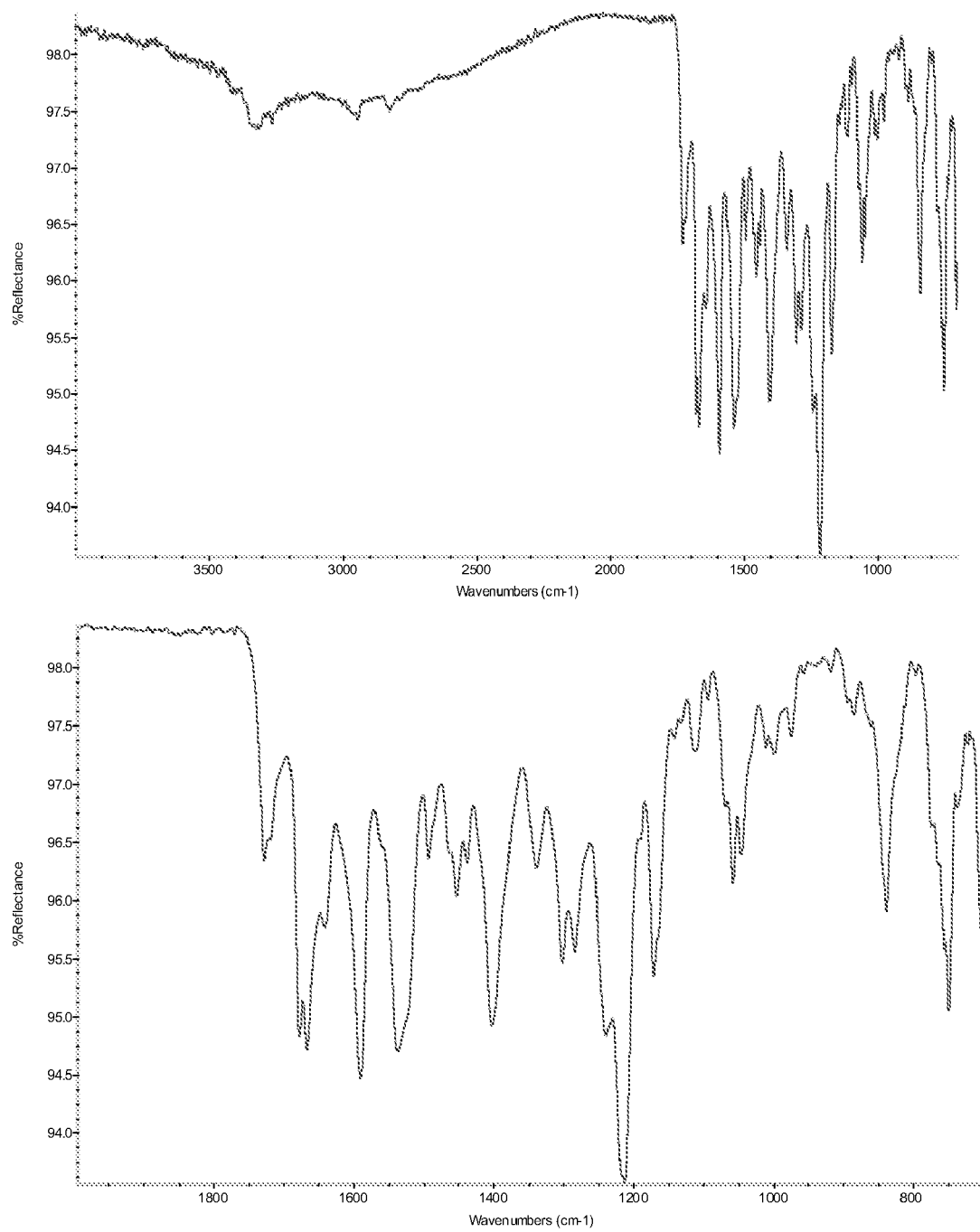
FIG. 8 shows an infrared (IR) absorption spectra of a sample of crystalline 1,2-succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester (Form 2).
Figure 9:
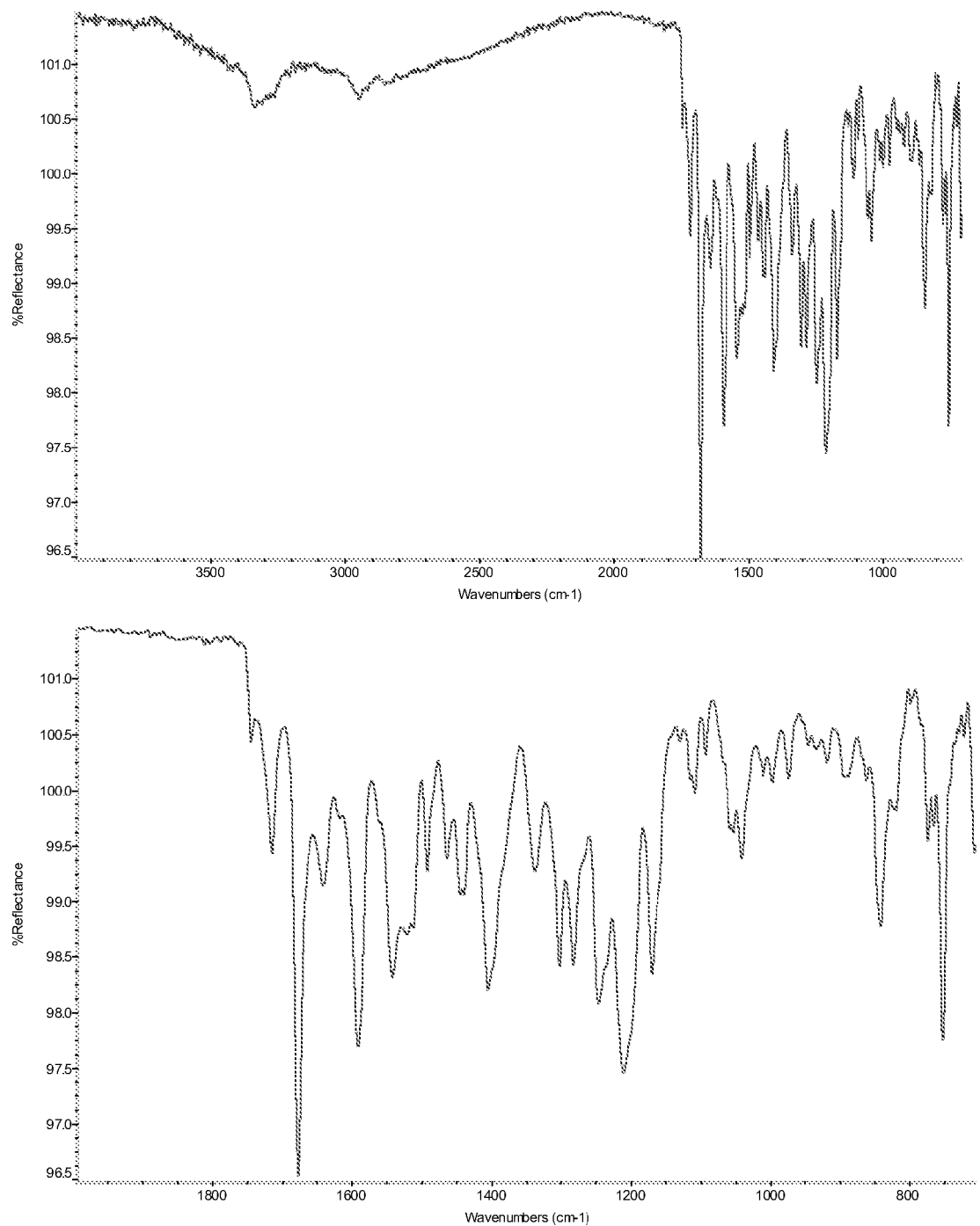
FIG. 9 shows an infrared (IR) absorption spectra of a sample of crystalline 1,2-succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester (Form 3).

The data for a representative sample of each of Forms 1, 2 and 3 is shown in FIGS. 7 to 9, respectively.

Example 10

Dynamic Vapour Sorption Assessment

A Dynamic Vapour Sorption (DVS) profile of Form 1 was obtained using an SMS DVS-1 with water as a reagent at 25° C. 20-30 mg of sample were placed in a glass bulb and equilibrated at 30% RH. The % RH was increased to 90% in 10% steps. The % RH was then decreased to 0% in 10% steps, and finally increased to 30% RH, again in 10% steps. The results of two sorption/desorption cycles are shown in FIG. 10

The DVS profile shows that the succinate salt, Form 1, has a reversible sorption/desorption profile with a good level of hygroscopicity (less than about 2.0% weight gain in the humidity range of 30% relative humidity to 90% relative humidity). The reversible moisture sorption/desorption profile demonstrates that the Form 1 succinate salt of the present invention possesses an acceptable hygroscopicity and is not deliquescent, thereby making it suitable for pharmaceutical development.

The invention claimed is:

1. A succinic acid salt of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, which is the Form 1 crystalline solid state form, wherein said salt is characterized by an x-ray powder diffraction pattern having diffraction peaks at 2θ values of 5.0±0.3 and 10.0±0.3.

2. The salt of claim 1, wherein the salt is further characterized by:
 (a) a differential scanning calorimetry trace which shows a melting point in the range of about 170° C. to about 180° C.; or
 (b) an infrared absorption spectrum with significant absorption bands at about 3265, 2832, 1735, 1718, 1679, 1669, 1591, 1540, 1518, 1493, 1439, 1405, 1339, 1302, 1283, 1239, 1202, 1163, 1144, 1107, 1095, 1039, 1009, 973, 921, 885, 868, 838, 773, 751, and 707 cm$^{-1}$.

3. The salt of claim 1 which is in micronized form.

4. A pharmaceutical composition comprising a pharmaceutically acceptable carrier and a salt of claim 1.

5. The pharmaceutical composition of claim 4, wherein the composition further comprises a steroidal anti-inflammatory agent.

6. The pharmaceutical composition of claim 5, wherein the steroidal anti-inflammatory agent is 6α,9α-difluoro-17α-[(2-furanylcarbonyl)oxy]-11β-hydroxy-16α-methyl-3-oxoandrosta-1,4-diene-17β-carbothioic acid S-fluoromethyl ester.

7. The pharmaceutical composition of claim 5, wherein the steroidal anti-inflammatory agent is fluticasone propionate.

8. The pharmaceutical composition of claim 4, in micronized form.

9. The pharmaceutical composition of claim 4, wherein the carrier is selected from the group consisting of lactose, starch, mannitol, dextrose, polylactic acid, polylactide-co-glycolide and a combination thereof.

10. A combination comprising:
(a) a salt of claim 1; and
(b) a steroidal anti-inflammatory agent.

11. The combination of claim 10, wherein the steroidal anti-inflammatory agent is 6α,9α-difluoro-17α-[(2-furanylcarbonyl)oxy]-11β-hydroxy-16α-methyl-3-oxoandrosta-1,4-diene-17β-carbothioic acid S-fluoromethyl ester.

12. The combination of claim 10, wherein the steroidal anti-inflammatory agent is fluticasone propionate.

13. A method of producing bronchodilation in a patient, the method comprising administering to the patient a bronchodilation-producing amount of a salt of claim 1.

14. A method of treating chronic obstructive pulmonary disorder or asthma, the method comprising administering to a patient in need of treatment a therapeutically effective amount of a salt of claim 1.

15. A process for preparing the Form 1 succinate salt according to claim 1, which process comprises the steps:
dissolving the succinate salt in aqueous THF, at a temperature in the range 18 to 23° C., adding a first volume of a lower alcohol to the aqueous THF;
heating the aqueous THF to 32-40° C.;
optionally seeding with Form 1;
adding a second volume of the lower alcohol to the heated aqueous THF,
cooling to the aqueous THF to a temperature in the range 18 to 23° C. to form a crystallized product; and
collecting the crystalline product.

* * * * *